United States Patent
Kogiso et al.

(10) Patent No.: US 10,905,764 B2
(45) Date of Patent: Feb. 2, 2021

(54) HYDRATED FOOD

(71) Applicant: Taiyokagaku Co., Ltd., Yokkaichi (JP)

(72) Inventors: Shizuka Kogiso, Yokkaichi (JP); Makoto Ozeki, Yokkaichi (JP); Nobuyuki Aoi, Yokkaichi (JP)

(73) Assignee: Taiyokagaku Co., Ltd., Yokkaichi (JP)

( * ) Notice: Subject to any disclaimer, the term of this patent is extended or adjusted under 35 U.S.C. 154(b) by 187 days.

(21) Appl. No.: 15/956,800

(22) Filed: Apr. 19, 2018

(65) Prior Publication Data

US 2018/0236083 A1    Aug. 23, 2018

Related U.S. Application Data

(63) Continuation of application No. 14/506,922, filed on Oct. 6, 2014, now abandoned, which is a continuation
(Continued)

(30) Foreign Application Priority Data

Apr. 28, 2005    (JP) ................. 2005-133107

(51) Int. Cl.
*A23L 33/10* (2016.01)
*A61K 47/22* (2006.01)
*A23L 27/00* (2016.01)
*A23L 33/175* (2016.01)
*A23L 33/18* (2016.01)
(Continued)

(52) U.S. Cl.
CPC ................ *A61K 47/22* (2013.01); *A23L 2/52* (2013.01); *A23L 2/60* (2013.01); *A23L 2/66* (2013.01); *A23L 27/70* (2016.08); *A23L 33/10* (2016.08); *A23L 33/175* (2016.08); *A23L 33/18* (2016.08);
(Continued)

(58) Field of Classification Search
None
See application file for complete search history.

(56) References Cited

U.S. PATENT DOCUMENTS 5,882,706 A    3/1999 Kawashima
5,922,380 A    7/1999 Takihara
(Continued)

FOREIGN PATENT DOCUMENTS

EP    1275308    1/2003
JP    57-170146 A1    10/1982
(Continued)

OTHER PUBLICATIONS

Pfeiffer P, Orben C, "*Pyroglutaminsaeure in Wein und Fruchtsaeften: Risiko und Vermeidung unerwuenschter Aromabeeinflussungen,*" Deutsche Lebensmittel-Rundschau, 2000, vol. 96, No. 1, pp. 4-8.
(Continued)

*Primary Examiner* — Felicia C Turner
(74) *Attorney, Agent, or Firm* — Burr & Brown, PLLC

(57) ABSTRACT

Providing a hydrated food which contains theanine and in which theanine content can stably be maintained even when the hydrated food is preserved for a long period of time and the taste threshold of the food can be improved and the peculiar taste can be flavored. The problem can be overcome by a hydrated food containing theanine and pyroglutamic acid. In this case, it is preferable that pH ranges from about 2.8 to about 7.5. Furthermore, it is preferable that a content of pyroglutamic acid ranges from about 1% to about 20% relative to a content of theanine.

4 Claims, 4 Drawing Sheets

Related U.S. Application Data of application No. 11/911,249, filed as application No. PCT/JP2006/308595 on Apr. 25, 2006, now abandoned.

(51) Int. Cl.
*A23L 33/185* (2016.01)
*A23L 2/52* (2006.01)
*A23L 2/60* (2006.01)
*A23L 2/66* (2006.01)
*A61K 31/195* (2006.01)

(52) U.S. Cl.
CPC .......... *A23L 33/185* (2016.08); *A61K 31/195* (2013.01); *A23V 2002/00* (2013.01)

(56) References Cited

U.S. PATENT DOCUMENTS

| | | |
|---|---|---|
| 6,589,566 B2 | 7/2003 | Ueda et al. |
| 6,719,963 B2 | 4/2004 | Parker |
| 2002/0169202 A1 | 11/2002 | Sakamoto et al. |
| 2004/0029955 A1 | 2/2004 | Kouge et al. |
| 2004/0241294 A1 | 12/2004 | Barabolak et al. |
| 2006/0211721 A1 | 9/2006 | Roberts |

FOREIGN PATENT DOCUMENTS

| | | |
|---|---|---|
| JP | 06-030757 A1 | 2/1994 |
| JP | 08-047383 A1 | 2/1996 |
| JP | 09-263573 A1 | 10/1997 |
| JP | 2001-299266 A1 | 10/2001 |
| JP | 2002-220335 A1 | 8/2002 |
| JP | 2004-018483 A1 | 1/2004 |
| JP | 2004-307453 A1 | 11/2004 |
| JP | 2005-278522 A1 | 10/2005 |

OTHER PUBLICATIONS

Masaki Tokuda et al., "*Kajitsu Yasai o Genzairyo to Shita Kako Yasai Juice Seizo Gijutsu no Kakuritsu*," Shiken Nendo Heisei 6, Nosuisanbutsu no Kako ni Kansuru Shiken Kenkyu Seisekishu 2 Kan, Yasai Kajitsu Hanarui ni Kansuru Shiken Kenkyu Seiseki, Showa 59 Nendo-Heisei 7 Nendo, 1997, pp. 70-74.

Shin'ichi Ozawa et al., "*Consomm Soup Kanetsu Chori ni Tomonau Yuri Amino Acid no Hendo*," The Japanese Society of Nutrition and Food Science Sokai Koen Yoshishu, 2004, 58th, p. 322.

Pfeiffer P, Orben C, "*Pyroglutaminsaeure in Wein und Fruchtsaeften: Risiko and Vermeidung unerwuenschter Aromabeeinflussungen*," Deutsche Lebensmittel-Rundschau, 2000, vol. 96, No. 1, pp. 4-8.

Mitomu Miyauchi et al, "*Onion Vinegar no Kinosei to Schokuhin eno Riyo*," New Food Industry, 2001, vol. 43, No. 10, pp. 36-38.

Park J-N et al., "*Chemical Composition of Fish Sauces Produced in Southeast and East Asian Countries*," Journal of Food Composition and Analysis, 2001, vol. 14, No. 2, pp. 113-125.

Eine Huttenen et al., "*Purification and Identification of Antimicrobial Substances Produced by Two Lactobacillus casei Strains*" 1995 International Dairy Journal, vol. 5, pp. 503-513.

Hiwatari et al., JP 09263573 Oct. 7, 1997, 2 pages (Year: 1997).

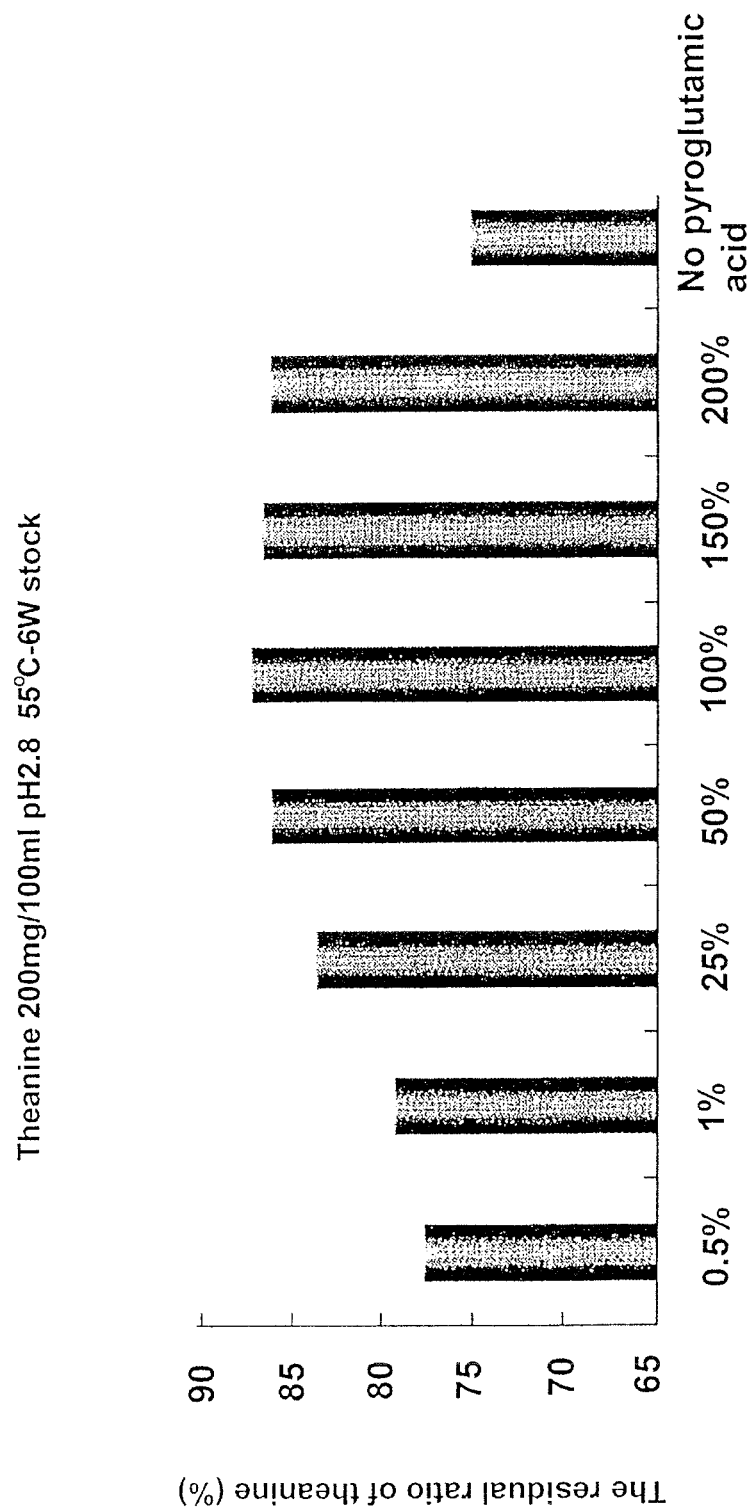

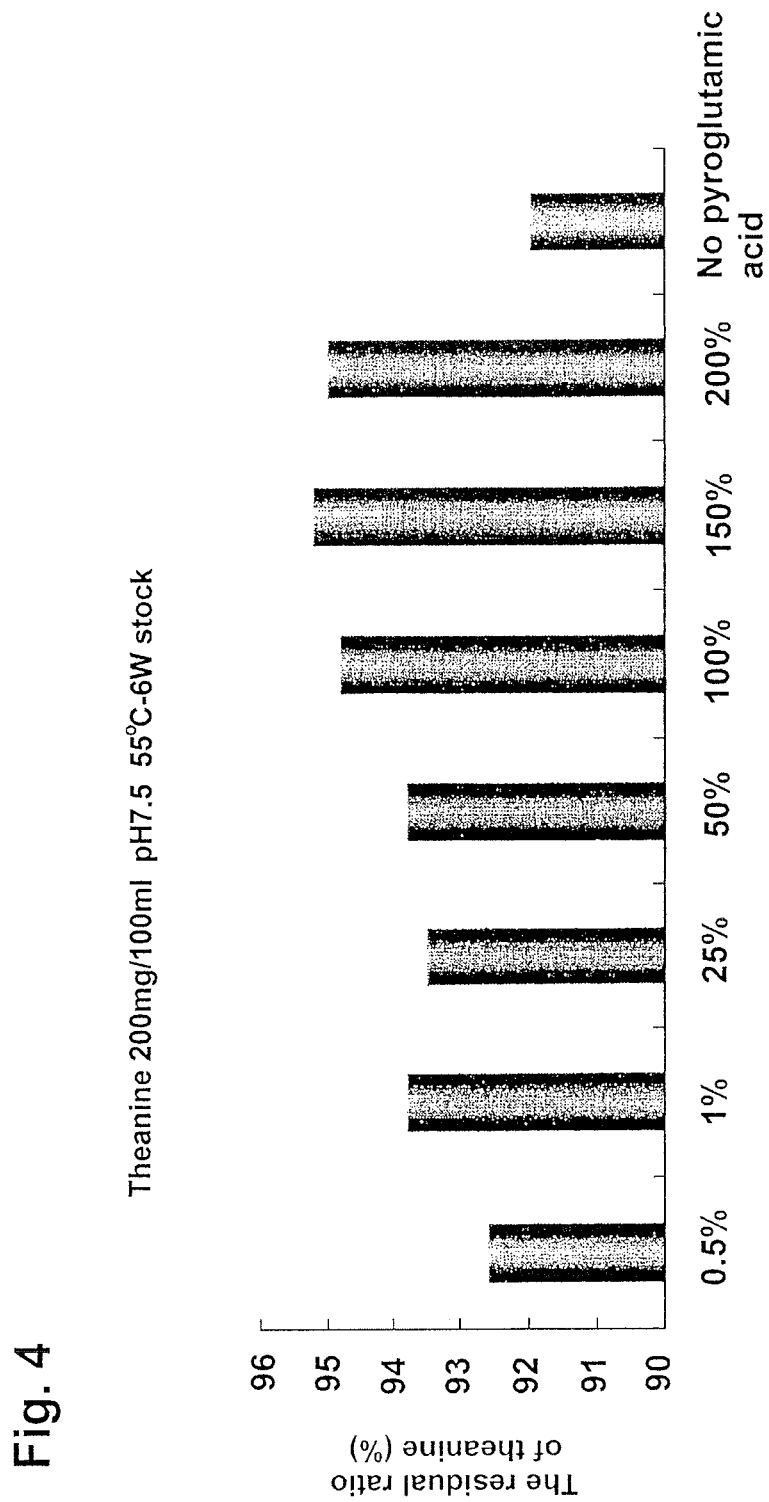

HYDRATED FOOD

CROSS-REFERENCE TO RELATED APPLICATIONS

This application is a continuation of U.S. application Ser. No. 14/506,922, filed Oct. 6, 2014, which in turn is a continuation of U.S. application Ser. No. 11/911,249, filed Sep. 10, 2008, which in turn is a National Stage application of PCT/JP2006/308595, filed Apr. 25, 2006, and claims the benefit under 35 USC § 119(a)-(d) of Japanese Patent Application No. 2005-133107, filed Apr. 28, 2005.

FIELD OF THE INVENTION

The present invention relates to a hydrated food containing as active ingredient pyroglutamic acid and theanine. Furthermore, the invention relates to a hydrated food which can stably maintain a content of theanine during preservation and improve a taste threshold by the presence of pyroglutamic acid in a solution of theanine, glutamine or glutamic acid. Still furthermore, the hydrated food can improve taste peculiar to branched chain amino acids, synthetic sweeteners and peptides.

BACKGROUND OF THE INVENTION

Theanine used in the present invention has effects of mood disorder curing, mind concentration improving, difficult menstruation suppression, flavor improvement composition and sleep facilitation, and thus, it is known that theanine has beneficial physiological effects. However, in order that the physiological effects may be experienced, 20 cups of tea need to be taken per occasion as an intake for adult. Accordingly, it is substantially impossible to take theanine from only tea. Development of a hydrated food containing theanine has been desired for the purpose of easily taking theanine. However, when theanine is preserved in a water-soluble liquid composition, theanine is decomposed with progress of time, whereupon there is a problem that a content of theanine is reduced when a hydrated food containing theanine is preserved for a long period of time.

Furthermore, when melted into a high concentrated state, theanine has its peculiar taste though theanine is a highly seasoned amino acid. Every taste has a threshold, which is the minimum concentration at which taste sensitivity to a particular substance or food can be perceived. Theanine has a threshold of 150 mg/100 ml, glutamine has a threshold of 250 mg/100 ml, and glutamic acid has a threshold of 5 mg/100 ml. Valine has a threshold of 150 mg/100 ml, leucine has a threshold of 380 mg/100 ml, and isoleucine has a threshold of 90 mg/100 ml. Taste is perceived when the concentration is equal to or higher than the threshold. The taste sometimes affects the hydrated food. Furthermore, acesulfame K, aspartame and L-phenylalanine all of which are synthetic sweeteners have respective unique bitterness. Some peptides also have bitterness at about 1000 mg/100 ml.

On the other hand, for example, patent document 1 discloses a technique for utilizing pyroglutamic acid as food. As disclosed, when pyroglutamic acid is contained in a frozen food, a period of time necessary for freezing and thawing the food is shortened and freezing denaturation of food can be suppressed. However, few things are generally known about the effects of pyroglutamic acids.

[Patent document] JP-A-H08-47383

SUMMARY OF THE INVENTION

An object of the present invention is to provide a hydrated food which contains pyroglutamic acid and theanine and in which a stable content of theanine can be maintained even when the hydrated food is preserved for a long period of time and which can increase the threshold of food and flavor the peculiar taste.

The inventors made repeated investigations in view of the above objects and found that the content of theanine in a hydrated food was stabilized by the use of pyroglutamic acid in the hydrated food containing theanine. In particular, when pH of the hydrated food ranges from about 2.8 to about 7.5, stable content of theanine can be maintained even though the hydrated food is a beverage or gel-food. Furthermore, the inventors found that the taste peculiar to theanine was reduced even in a solution in which theanine more than a threshold of amino acid is dissolved and food having bitterness could be flavored, thereby basically made the invention.

More specifically, the present invention is each of the following (1) to (5):

(1) A hydrated food characterized by containing (A) pyroglutamic acid;

(2) A hydrated food characterized by containing one or more amino acids selected from groups comprising (A) pyroglutamic acid, (B) theanine, glutamine and glutamic acid;

(3) A hydrated food characterized by containing one or more amino acids selected from groups comprising (A) pyroglutamic acid, (B) theanine, glutamine and glutamic acid, and (C) branched chain amino acid;

(4) A hydrated food characterized by containing one or more amino acids selected from groups comprising (A) pyroglutamic acid, (B) theanine, glutamine and glutamic acid, and one or more synthetic sweeteners selected from a group of (D) acesulfame K, aspartame and L-phenylalanine;

(5) A hydrated food characterized by containing one or more amino acids selected from groups comprising (A) pyroglutamic acid, (B) theanine, glutamine and glutamic acid, and (E) peptide;

(6) The hydrated food according to any one of (1) to (5), characterized in that the hydrated food is a beverage having pH ranging from about 2.8 to about 7.5; and (7) The hydrated food according to any one of (1) to (5), characterized in that the hydrated food is a gel food having pH ranging from about 2.8 to about 7.5.

A pyroglutamic acid used in the present invention is also known as pyrrolidone carboxylic acid (2-pyrrolidone-5-carboxylic acid) and is a derivative of amino acid having a molecular formula of $C_5H_7NO_3$ and a molecular weight of 129. The substance is present in sufficient quantity in Steffen's Waste which is a byproduct in the manufacture of sugar beet. When L-glutamic acid is hydrolyzed at 175° C., partially racemized pyroglutamic acid is obtained. Furthermore, when L-glutamic acid-γ-methyl ester or L-glutamic acid-γ-ethyl ester is left in methanol saturated with ammonia, optically pure pyroglutamic acid can readily be obtained. The obtained pyroglutamic acid has a rhombic column crystal and a melting point ranging from 159° C. to 160.5° C., and is an easily water-soluble substance.

Pyroglutamic acids have conventionally been used as seasoning (JP-A-2001-299266) and sound hair agent (JP-A-2001-81013). However, applications to stabilization of beverage and flavoring have been unknown.

The pyroglutamic acid used in the present invention can be used as salt. The salt should not be limited to a specific one and monovalent, bivalent or trivalent salt can be used. In particular, it is preferable to use monovalent salt (preferably, potassium chloride or sodium chloride).

A pyroglutamic acid obtained by any method is available as the pyroglutamic acid used in the present invention. For example, the pyroglutamic acid may be extracted from a plant such as sugar beet or isolated from a hot-water extract of various animals or may be a derivative from glutamic acids, glutamine or the like.

The pyroglutamic acid used in the present invention has a content ranging from about 0.0003% to about 40% relative to total mass of the hydrated food.

Theanine used in the present invention is known as a principal component of deliciousness of green tea and is an important substance as a flavor component of food such as tea. Methods of making theanine used in the invention include a method of extracting theanine form tea leaves, a method of obtaining theanine by organic synthesis reaction (Chem. Pharm. Bull. 19 (7) 1301-1307 (1971)), a method of causing glutaminase to react against a mixture of glutamine and ethylamine thereby to obtain theanine (JP-B-H07-55154), a method of culturing culture cells of tea in a culture medium containing ethylamine and facilitating growth of culture cells while an amount of theanine stored in the culture cells is being increased (JP-A-H05-123166), substituting ethylamine derivative such as monoethylamine hydrofluoride for ethylamine, thereby obtaining theanine (JP-A-2000-026383) and the like. Theanine may be obtained from any one of the above-described methods. Green tea, oolong tea, tea and the like are exemplified as the leaves of tea. Any one of L-, D- and DL-theanine may be used. L-theanine is preferable in the invention since it is particularly recognized as food additives and is economic in use.

Furthermore, the theanine used in the invention may be any one of a refined product containing 98% or more of theanine, rough refined product with content of theanine ranging from 50% to 98% and extract with content of theanine ranging from 10% to 50%.

Theanine used in the invention has a high security. For example, in an acute toxicity test with use of mice, no mice died and abnormality was found in an ordinary state, weight and the like even in the case of oral administration of theanine by 5 g/kg. Furthermore, theanine is known as a principal component of deliciousness of tea and used as a food additive for use as gustatory. An amount of theanine to be added is not limited under the Food Sanitation Law.

Glutamine in the present invention is a 2-aminoglutalamid acid and becomes glutamic acid by acid hydrolysis. Glutamine is classified into polar non-charged side-chain amino acids or neutral polar side-chain amino acids. Glutamine is one of amino acids composing protein which is contained in a large amount in extracellular fluid of animals and is a non-essential amino acid. However, since a rise of catabolism such as metabolic stress sometimes renders an amount of glutamic biosynthesis in the body short, glutamine is treated as quasi-essential amino acid. Glutamine in the invention is synthesized from glutamic acid by the action of glutamine synthetase (glutamic acid ammonia ligase, EC 6.3.1.2). However, glutamine may be manufactured by another manufacturing method.

Glutamine in the present invention is a 2-aminoglutalamid acid and was first found from hydrolysate of wheat gluten. Monosodium glutamate (MSG) which is sodium salt of glutamic acid is used as a chemical seasoning. Glutamic acid is classified into acidic polar side-chain amino acids. Glutamic acid is one of amino acids composing protein and a non-essential amino acid. Glutamic acid also functions as a neurotransmitter in animal bodies. A sea tangle, cheese, green tea and the like are known to contain a large amount of glutamic acid. A mushroom, tomato, sea food and the like are also known to contain a large amount of glutamic acid.

Glutamic acid in the invention is synthesized by causing 2-oxoglutaric acid in a citric acid cycle to receive an amino group from another amino acid by the action of glutamic transferase or by reverse reaction of degradation of glutamic acid into 2-oxoglutaric acid and ammonia by glutamate dehydrogenase (EC 1.4.1.3). Glutamic acid is primarily used for manufacture as an intermediate material of monosodium glutamate which is a food additive. Since glutamic acid itself has acidity, neutralized sodium salt is used as a seasoning.

Glutamic acid in the invention may be obtained by any one of methods of producing by amino-acid fermentation of microbe with molasses or rice, cornstarch and ammonium chloride serving as materials; obtaining by adding hydrochloric acid to vegetable albumin such as soybean albumin or gluten and hydrolyzing the addition in a high temperature atmosphere; extracting, by the Steffen process, waste molasses produced in the process of making beet sugar from beet; separating L-glutamic acid from DL-glutamic acid obtained by carboxylation, cynoamin, or hydration of acrylonitrile as a material; and amino-acid fermentation of microbe by the action of coenzyme and enzyme such as glutamate dehydrogenase, amino transferase or the like with molasses or rice, cornstarch and ammonium chloride serving as materials.

Branched amino acid in the invention is Valine, leucine or isoleucine. The branched amino acid has a structure that a chain of carbon (methyl group: —$CH_3$) is branched. These three amino acids are named generically "branched chain amino acid" (BCAA). The branched chain amino acid is an essential amino acid and occupies about 50% of essential amino acids contained in food protein and about 35% of essential amino acids contained in protein of muscle. Furthermore, the branched chain amino acid performs an important role as a material for muscles (protein) of a human body and as an energy source during physical activities. The branched chain amino acid is metabolized in muscles. Upon a hard physical activity, glucide is first used as an energy source. When the glucide has been consumed, protein in muscles is decomposed into branched chain amino acids, which are used as an energy source.

Thus, the branched chain amino acid is easy to be converted to energy. It is known that the branched chain amino acid suppresses reduction in muscles and muscle weakness, makes up for stamina and increases endurance. Furthermore, it is known that the branched chain amino acid has effects of smoothly reproducing muscles and suppressing a value of blood lactic acid as a fatigue-producing substance to prevent muscular fatigue and suppressing increase in serotonin as neurotransmitter in the brain to prevent tired feeling and reduction in vigor and powers of concentration. Valine of the branched chain amino acid is known to have functions of adjustment of nitrogen balance, promotion of growth and adjustment of nervous system as well as metabolic promotion and a function as energy source. Leucine promotes synthesis of skin, bone and muscle and suppresses degradation of muscular organization and accordingly has effects of recovering from fatigue, increasing the physical strength, improving liver functions and adjusting blood glucose level. Isoleucine is known to have effects of promoting growth, adjusting functions of nerve system, expanding blood vessels and improving liver functions.

Acesulfame K (acesulfame potassium) is an artificial sweetener made from a material of "diketene" which is also used as dyes and pigments and synthetic material of pharmaceuticals. Acesulfame K is 200 times sweeter than sugar and has a high heat resistance and is stable. Acesulfame K received approval as a food additive in 2000 in Japan.

Aspartame in the invention is an ester of aspartic acid, phenylalanine and methanol and is about 200 times sweeter than sugar.

L-phenylalanine in the invention is a glycogenic essential amino acid and is known to become a synthetic material for a neurotransmitter of noradrenaline and dopamine in the brain. These synthetic sweeteners have peculiar bitterness as an aftertaste.

Peptide in the invention is a polymer of two or more amino acids and is obtained by synthesis or degradation of protein. The peptide is natural or synthetic and contains hydrolysate of protein and fraction thereof. The peptide is a simple or a mixture of them or a mixture of amino acid and peptide.

As the hydrated food of the invention is exemplified a preferred beverage, refreshing beverage, carbonated beverage, fruit beverage, lactic acid drink, lactic beverage, sports drink, diet drink, supplementary beverage, alcohol-containing beverage, liquid beverage or solid ferry both made by blending gelatinizing agent and the like. The hydrated food of the invention, should not be limited particularly, designates all the beverages containing water. A water content should not be limited and is normally not less than 50%, preferably not less than 80%, more preferably not less than 90%, and most preferably not less than 90%.

The hydrated food of the invention has pH ranging from about 2.8 to about 7.5, preferably ranging from about 4.3 to about 7.0, further preferably ranging from about 5.0 to about 6.0. The pH is adjusted in the range so that a content of theanine in the hydrated food is easy to be maintained stably for a long period of time. A pH adjusting agent should not be limited. For example, as the pH adjusting agent can be used a food additive such as a citric acid, malic acid, tartaric acid, phosphoric acid, maleic acid, ascorbic acid or acetic acid and a natural substance such as lemon.

The hydrated food of the invention contains theanine whose concentration ranges from about 0.03 mg/mL to about 250 mg/mL, preferably ranges from about 0.3 mg/mL to about 250 mg/mL, more preferably ranges from about 1.5 mg/mL to about 250 mg/mL. When the concentration exceeds 250 mg/mL, the theanine cannot be dissolved since the value is an upper limit of dissolution.

Pyroglutamic acid and theanine both contained in the hydrated food of the invention have a mass ratio (that is, pyroglutamic acid/theanine) ranging from about 0.1% to about 200%, preferably ranges from about 0.5° to about 100%, more preferably ranges from about 5% to about 50%. When such an amount of pyroglutamic acid is added to the hydrated food, the theanine can stably be maintained at a predetermined content for a long period of time, whereupon a taste peculiar to theanine is easy to reduce.

In order that glutamine may be flavored in the hydrated food of the invention, pyroglutamic acid and glutamine have a mass ratio (that is, pyroglutamic acid/glutamine) ranging from about 0.05% to about 100%, preferably ranges from about 0.1% to about 50%, more preferably ranges from about 1% to about 30%. When such an amount of pyroglutamic acid is added to the hydrated food, a taste peculiar to glutamine is easy to reduce.

In order that glutamic acid may be flavored in the hydrated food of the invention, pyroglutamic acid and glutamic acid have a mass ratio (that is, pyroglutamic acid/glutamic acid) ranging from about 3% to about 6000%, preferably ranges from about 15% to about 3000%, more preferably ranges from about 150% to about 1500%. When such an amount of pyroglutamic acid is added to the hydrated food, a taste peculiar to glutamine is easy to reduce.

In order that valine acid may be flavored in the hydrated food of the invention, pyroglutamic acid and valine have a mass ratio (that is, pyroglutamic acid/valine) ranging from about 0.1% to about 200%, preferably ranges from about 0.5% to about 100%, more preferably ranges from about 5% to about 50%. When such an amount of pyroglutamic acid is added to the hydrated food, a bitter taste peculiar to valine is easy to reduce.

In order that glutamic acid may be flavored in the hydrated food of the invention, pyroglutamic acid and leucine have a mass ratio (that is, pyroglutamic acid/leucine) ranging from about 0.03% to about 80%, preferably ranges from about 0.2% to about 40%, more preferably ranges from about 2% to about 20%. When such an amount of pyroglutamic acid is added to the hydrated food, a bitter taste peculiar to glutamine is easy to reduce.

In order that isoleucine may be flavored in the hydrated food of the invention, pyroglutamic acid and isoleucine have a mass ratio (that is, pyroglutamic acid/isoleucine) ranging from about 0.1% to about 300%, preferably ranges from about 1% to about 200%, more preferably ranges from about 10% to about 100%. When such an amount of pyroglutamic acid is added to the hydrated food, a bitter taste peculiar to valine is easy to reduce.

In order that acesulfame K may be flavored in the hydrated food of the invention, pyroglutamic acid and acesulfame K have a mass ratio (that is, pyroglutamic acid/acesulfame K) ranging from about 100% to about 10000%, preferably ranges from about 50% to about 5000%, more preferably ranges from about 10% to about 1000%. When such an amount of pyroglutamic acid is added to the hydrated food, a bitter taste peculiar to acesulfame K is easy to reduce.

In order that aspartame may be flavored in the hydrated food of the invention, pyroglutamic acid and aspartame have a mass ratio (that is, pyroglutamic acid/aspartame) ranging from about 100% to about 10000%, preferably ranges from about 50% to about 5000%, more preferably ranges from about 10% to about 1000%. When such an amount of pyroglutamic acid is added to the hydrated food, a bitter taste peculiar to aspartame is easy to reduce.

In order that L-phenylalanine may be flavored in the hydrated food of the invention, pyroglutamic acid and L-phenylalanine have a mass ratio (that is, pyroglutamic acid/L-phenylalanine) ranging from about 10% to about 1000%, preferably ranges from about 5% to about 500%, more preferably ranges from about 1% to about 100%. When such an amount of pyroglutamic acid is added to the hydrated food, a bitter taste peculiar to L-phenylalanine is easy to reduce.

In order that peptide may be flavored in the hydrated food of the invention, pyroglutamic acid and peptide have a mass ratio (that is, pyroglutamic acid/peptide) ranging from about 1% to about 800%, preferably ranges from about 5% to about 400%, more preferably ranges from about 10% to about 200%. When such an amount of pyroglutamic acid is added to the hydrated food, a bitter taste peculiar to L-phenylalanine is easy to reduce.

The hydrated food of the invention may contain simple sugar used in ordinary foods or the like, nonreducing sugar, natural sweetener, artificial sweetener, polysaccharide, food fiber and gelling agent. For example, one is selected and used from the following: pentose such as glucose, fructose, galactose, mannose, ribose, deoxyribose and the like; hexose such as glucose, fructose, galactose and the like; arabinose, sucrose, purified sucrose, lactose, sweet tea, fructose, low-fructose corn syrup, high-fructose syrup, high-fructose corn syrup, starch syrup, muscovado, honey, refined honey, isomerized sugar syrup, simple syrup, trehalose, erythritol, sorbitol, maltitol, palatinose, xylitol, sucralose, saccharin, saccharin sodium, glycyrrhizic acid, monoammonium glycyrrhizinate, diammonium glycyrrhizinate, dipottasium glycyrrhizinate, disodium glycyrrhizinate, triammonium glycyrrhizinate, oligosaccharide, carrageenan, agar, gelatin, pectine, xanthan gum, algin acid, alginate solutions, CMC, or the like.

The hydrated food of the invention may generally contain flavoring substances used in a food or the like. As such flavoring substances are exemplified various types of flavors, for example, lemon flavor, orange flavor, grapefruit flavor, chocolate flavor, dl-menthol, l-menthol or the like.

Furthermore, the hydrated food of the invention may be used with natural medicines, herbs, amino acids, peptide, vitamins, minerals, other foods, materials allowed as pharmaceutical products. There is no specific limitation to such natural medicines. However, for example, the natural medicines may include valenian, angelicae radix, paeoniae radix, tree peony, ginseng, etc.

There is no specific limitation to the amino acid to be used. However, for example, the amino acid may include glycine, alanine, praline, hydoxyproline, histidine, arginine, lysine, hydroxylysine, tyrosine, tryptophan, asparagines, asparagine acid, glutamine, glutamic acid, hydoxyproline, serine, threonine, methionine, cysteine, natural or synthetic cystine There is no specific limitation to the herb. However, for example, the herb may include anise, carrot seed, cloves, coriander, cypress, cinnamon, juniper, ginger, sweet orange, basil, patchouli, bitter orange, fennel, black pepper, bay, peppermint, bergamot, mandarin, myrrh, lemon grass, rosemary, vanilla, hyssop, eucalyptus, lime, lemon, ylangylang, cardamom, clarysage, jasmine, geranium, Bulgarian rose, rose, olibanum, matricaria, sandalwood, verbena, petit grain, vetivera zizanoides, marjoram, *Melissa officinelis*, rosewood, *Hypericum*, St. Jones Wart and kava kava.

There is no specific limitation to the vitamin. However, for example, the vitamin may include vitamin A, vitamin B1, vitamin B2, vitamin B6, vitamin B12, vitamin C, vitamin D, vitamin E, vitamin K, folic acid, niacin, lipoic acid, pantothenic acid, biotin and ubiquinone. Vitamin B1, B6 and B12 are more preferable. Furthermore, the vitamins include the derivatives thereof.

There is no specific limitation to the mineral. However, for example, the mineral may include calcium, iron, magnesium, copper, zinc, selenium and potassium.

Furthermore, the following material may be used with the tablet of the invention: aloe, royal jelly, placenta, propolis, isoflavone, soy isoflavone, egg yolk lecithin, lecithin, chondroithin, cacao mass, collagen, vinegar, chlorella, spirulina, ginkgo leaf, green tea, hardy rubber tree, oolong tea, mulberry leaf, *Rubus suavissimus, Lagerstroemia speciosa*, unsaturated fatty acid, saccharide such as sugar alcohol and oligosaccharide, fungi such as *bifidus bacillus*, mushrooms such as *agaricus, agaricus* blazei Murrill, blacket fungus of the genus *Fores, Grifola frondose*, fruit such as blueberry, prune, grape, olive and plum, molokheiya such as peanut, almond, sesame and pepper, vegetables such as green pepper, cayenne pepper, welsh onion, pumpkin, gourd, carrot, burdock, molokheiya, garlic, beefsteak plant, Japanese horseradish, tomato, scallion, leaf vegetables, sweet potato and beans, seaweeds such as "wakame" seaweed, fish and shellfish, meat of beast, birds and whales and grains. Furthermore, usable are extracts, dried products, coarse product, refined product, processed product and distilled product.

The hydrated food of the invention may include oral foods such as beverages, jelly or the like manufactured by dispensing artificial colorant, preservative, antioxidant, thickening/stabilization agent, emulsifier, gelling agent or the like usually used in food manufacture, if necessary.

The hydrated food of the invention may include necessary foodstuff such as lipid, electrolyte or the like other than aforesaid acidifiers, sweeteners, amino acids, fragrant materials, herbs, vitamins and mineral.

According to the present invention, the dehydrated food can be provided which is superior in a long period preservation and stability of theanine and can improve a taste threshold of food and flavor the food with respect to peculiar taste.

BRIEF DESCRIPTION OF THE DRAWINGS

FIG. 3 is a graph showing the residual ratio of theanine after the preservation test with respect to pH 2.8 theanine solution to which pyroglutamic acid ranging from 0% to 200% is added; and FIG. 4 is a graph showing the residual ratio of theanine after the preservation test with respect to pH 7.5 theanine solution to which pyroglutamic acid ranging from 0% to 200% is added.

DETAILED DESCRIPTION OF THE INVENTION

Figure 1:
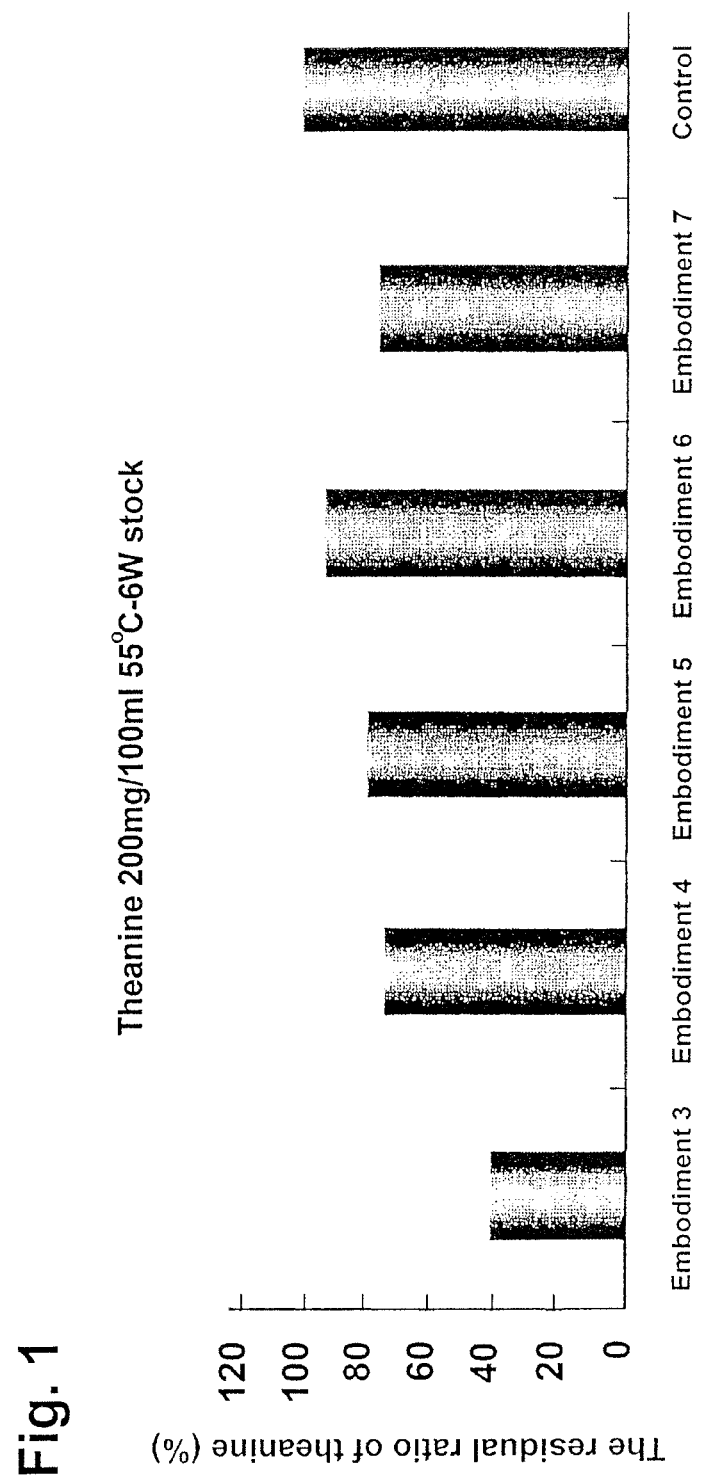
FIG. 1 is a graph showing the residual ratio of theanine after the preservation test with respect to theanine solutions of embodiments 3 to 7.

Embodiments of the present invention will be described in detail. However, the technical scope of the invention should not be limited by the following description of embodiments but can be practiced in various modified forms. Furthermore, it is noted that the technical scope of the invention should encompass the scope of equivalence.

<Embodiment 1> Manufacture of Theanine by Enzyme Method 0.3 M glutamine and 1.5 M methylamine hydrochloride were reacted in the presence of 0.3 U glutaminase (commercially available) at 30° C. for 22 hours in a buffer solution of 0.05 M boric acid (pH 11), whereby 225 nm theanine was obtained. Reaction liquid was applied to Dowex 50×8 columnar chromatography and Dowex 1×2 columnar chromatography (both made by Muromachi Chemical Co., Ltd.) thereby to be processed by ethanol, whereby an object substance is isolated from the reaction liquid.

The isolated substance was applied to an amino acid analyzer (made by Hitachi Co.) and paper chromatography. Since the isolated substance behaved in the same way as a standard substance, it was recognized as L-theanine. When the isolated substance was processed by hydrolysis using hydrochloric acid or glutaminase, glutamine acid and ethylamine were produced in a ratio of 1:1. Thus, since the isolated substance was hydrolyzed by glutaminase, it was shown that ethylamine was γ-ethylamine of glutamine acid. Furthermore, it was confirmed on the basis of glutamate dehydrogenase that glutamine acid produced by hydrolysis was L-glutamine acid. As a result, 8.5 g theanine was obtained.

<Embodiment 2> Extraction of Theanine from Tea Leaves 10 kg tea leaf (*Camellia sinensis*) was extracted using heated water and thereafter, the obtained extract was passed through a cation exchange resin (type HCR W-2 made by Muromachi Chemical Industry Co., Ltd.) so as to be eluted by 1N NaOH. Eluted fraction was passed through activated charcoal (Taiko activated charcoal SG made by Futamura Chemical Industry Co., Ltd. The fraction eluted by 15% ethanol was concentrated using an RO film (type NTR 729 HF made by Nitto Denko Corporation). The concentrated eluted fraction was refined by columnar chromatography and then re-crystallized such that 24.8 g theanine was obtained.

L-theanine (product name: Suntheane made by Taiyo Kagaku Co., Ltd.) and valine (manufactured by Ajinomoto Co. Inc.) were used in the following experiments and production of each composition.

<Embodiment 3> Theanine Solution Preparation 1

10 mM citric acid solution and acetic acid were suitable mixed together and prepared so that pH of the mixture became 2.0. 200 mg L-theanine was added to 100 mL of the prepared solution to be dissolved and thereafter passed through a 0.45 μm filter, whereby 2 mg/mL L-theanine solution with pH of 2.0 was prepared.

<Embodiment 4> Theanine Solution Preparation 2

10 mM citric sodium solution and 10 mM citric acid solution were suitably mixed together to be prepared so that pH of the mixture became 2.8, whereby a citric buffer fluid was prepared. 200 mg of L-theanine was added to 100 mL of the buffer fluid to be dissolved and thereafter passed through a 0.45 μm filter, whereby 2 mg/mL L-theanine solution with pH of 2.8 was prepared.

<Embodiment 5> Theanine Solution Preparation 3

10 mM citric sodium solution and 10 mM citric acid solution were suitably mixed together to be prepared so that pH of the mixture became 4.3, whereby a citric buffer fluid was prepared. 200 mg of L-theanine was added to 100 mL of the buffer fluid to be dissolved and thereafter passed through a 0.45 μm filter, whereby 2 mg/mL L-theanine solution with pH of 4.3 was prepared.

<Embodiment 6> Theanine Solution Preparation 4

10 mM citric sodium solution and 10 mM citric acid solution were suitably mixed together to be prepared so that pH of the mixture became 5.5, whereby a citric buffer fluid was prepared. 200 mg of L-theanine was added to 100 mL of the buffer fluid to be dissolved and thereafter passed through a 0.45 μm filter, whereby 2 mg/mL L-theanine solution with pH of 5.5 was prepared.

<Embodiment 7> Theanine Solution Preparation 5

3 N hydrochloric acid was added to 10 mM sodium dihydrogen phosphate solution and prepared so that pH of the solution became 7.5. 200 mg L-theanine was added to 100 mL of the prepared solution to be dissolved and thereafter passed through a 0.45 μm filter, whereby 2 mg/mL L-theanine solution with pH of 7.5 was prepared.

<Embodiment 8> Theanine Solution Preparation 6

10 mM citric sodium solution and 10 mM citric acid solution were suitably mixed together to be prepared so that pH of the mixture became 4.3, whereby a citric buffer fluid was prepared. 10 mg, 50 mg, 100 mg, 200 mg, 400 mg and 600 mg of L-theanine was each added to 100 mL of the buffer fluid to be dissolved and thereafter passed through a 0.45 μm filter, whereby 0.1 mg/mL, 0.5 mg/mL, 1 mg/mL, 2 mg/mL and 4 mg/mL and 6 mg/mL L-theanine solution with pH of 4.3 was prepared.

<Embodiment 9> Pyroglutamic-Acid Containing Theanine Solution Preparation 1

0%, 0.5%, 1%, 25%, 50%, 100%, 150% and 200% pyroglutamic acid was added to the theanine solution of embodiment 4 with pH of 2.8 relative to theanine and dissolved and agitated, and thereafter passed through a 0.45 μm filter, whereby pyroglutamic-acid containing theanine solution with pH of 2.8 was prepared. The pyroglutamic acid was made by AJINOMOTO CO., INC.

<Embodiment 10> Pyroglutamic-Acid Containing Theanine Solution Preparation 2

0%, 0.5%, 1%, 25%, 50%, 100%, 150% and 200% pyroglutamic acid was added to the theanine solution of embodiment 4 with pH of 7.5 relative to theanine and dissolved and agitated, and thereafter passed through a 0.45 μm filter, whereby pyroglutamic-acid containing theanine solution with pH of 7.5 was prepared.

<Embodiment 11> Determination of Quantity of Theanine by HPLC

Theanine content in theanine solution prepared in each embodiment was determined using a high performance liquid chromatography (HPLC). Conditions of quantitative determination of HPLC are shown by the following table.

TABLE 1

| | |
|---|---|
| Column | Develosil ODS HG-5/Nomura Kagaku Co., LTD. |
| Detector | Waters 2487 dual λ UV/VIS detector/Waters Co., LTD. |
| Theanine standard | L-theanine/Kurita Kogyo Co., LTD. |
| internal standard | Nicotineamide/Nakaraitesuku Co., LTD. |
| mobile phase | water:methanol:TFA = 980:20:1 |

<Embodiment 12> Preparation of Beverage

A pyroglutamic-acid added beverage was prepared using components as shown in the following TABLE 2. More specifically, to 8 L purified water were agitated and dissolved L-theanine, guagum degradation product (trade name: "Sunfiber HG" made by TAIYO KAGAKU CO., LTD.), pyroglutamic acid, DL-malic acid, granulated sugar, low-fructose corn syrup and ⅕ concentrated apple juice while being sequentially added to. Fragrance, citric sodium and purified water were added to the solution so that pH became 4.5. A total quantity of solution was set to 10 L and thereafter passed through a 0.22 µm sterilization filter. The solution was put into bistered bottles each having a content of 100 mL. A beverage containing 400 mg L-theanine per bottle was produced. Furthermore, a beverage containing no pyroglutamic acid was also produced.

TABLE 2

| Component | pyroglutamic acid (—) (percent by mass) | pyroglutamic acid 0.1% (percent by mass) |
|---|---|---|
| L-theanine | 0.4 | 0.4 |
| pyroglutamic acid | — | 0.1 |
| guagum degradation product | 1.0 | 1.0 |
| DL-malic acid | 0.05 | 0.05 |
| granulated sugar | 2.0 | 2.0 |
| low-fructose corn syrup | 3.0 | 3.0 |
| ⅕ concentrated apple juice | 0.2 | 0.2 |
| fragrance | 0.1 | 0.1 |
| citric sodium | pH adjuster | pH adjuster |
| purified water | a proper amount | a proper amount |

<Embodiment 13> Preparation of Jelly Beverage

A jelly beverage added with pyroglutamic-acid was prepared using composition as shown in the following TABLE 3. More specifically, with purified water were mixed a gelling agent (trade name: "Neosoft DAR" made by TAIYO KAGAKU CO., LTD.), L-theanine, pyroglutamic acid, granulated sugar and maltose water candy. The mixture was heated at 85° C. and dissolved and thereafter, mango puree, ⅕ concentrated lemon juice, fragrance and citric sodium were added to the mixture and prepared to pH of 4.5. The prepared mixture was processed by one-minute plate sterilization at 94° C., filtrated by the use of a 100-mesh filter and thereafter put into flexible pouches, whereby the jelly beverage was prepared. Furthermore, another jelly beverage added with no pyroglutamic acid was made as a comparative example.

TABLE 3

| Component | pyroglutamic acid (—) (percent by mass) | pyroglutamic acid 0.1% (percent by mass) |
|---|---|---|
| gelling agent | 0.5 | 0.5 |
| L-theanine | 0.2 | 0.2 |
| pyroglutamic acid | — | 0.1 |
| granulated sugar | 3.0 | 3.0 |
| maltose water candy | 25.0 | 25.0 |
| mango puree | 20.0 | 20.0 |
| ⅕ concentrated lemon juice | 0.3 | 0.3 |
| fragrance | 0.1 | 0.1 |
| citric sodium | pH adjuster | pH adjuster |
| purified water | a proper amount | a proper amount |

<Test Example 1> Preservation Test

Theanine solution of each of embodiments 3 to 10 was put into a transparent and colorless vial every 20 mL and preserved in an incubator at 55° C. for six weeks.

Furthermore, the beverage of embodiment 12 and jelly beverage of embodiment 13 were also preserved in the incubator at 55° C. for six weeks.

<Test Example 2> Comparison of Stability in Content of Theanine with Different pH's Samples of the theanine solutions of embodiments 3 to 7 were preserved in the manner of preservation test of test example 1 and evaluated by the theanine measurement method described in embodiment 11. FIG. 1 shows theanine content in the solution of each embodiment after end of the preservation test.

As shown in the figure, after end of the preservation test, the concentration of theanine solution of embodiment 3 was reduced to about 40% of an initially loaded quantity (2 mg/mL) and accordingly lacked for stability. The concentration of theanine solution of embodiment 4 after the end of preservation test was reduced to about 74% of the initially loaded quantity. The concentration of theanine solution of embodiment 5 was reduced to about 80%. The concentration of theanine solution of embodiment 6 was reduced to about 90%. When compared with the results of the solution of embodiment 3, each embodiment was improved in the stability of theanine. The solution of embodiment 7 was reduced to about 76% of the initially loaded quantity and was more stable as compared with the solution of embodiment 3.

<Test Example 3> Comparison of Stability with Changes in Theanine Concentration (pH 4.3)

Figure 2:
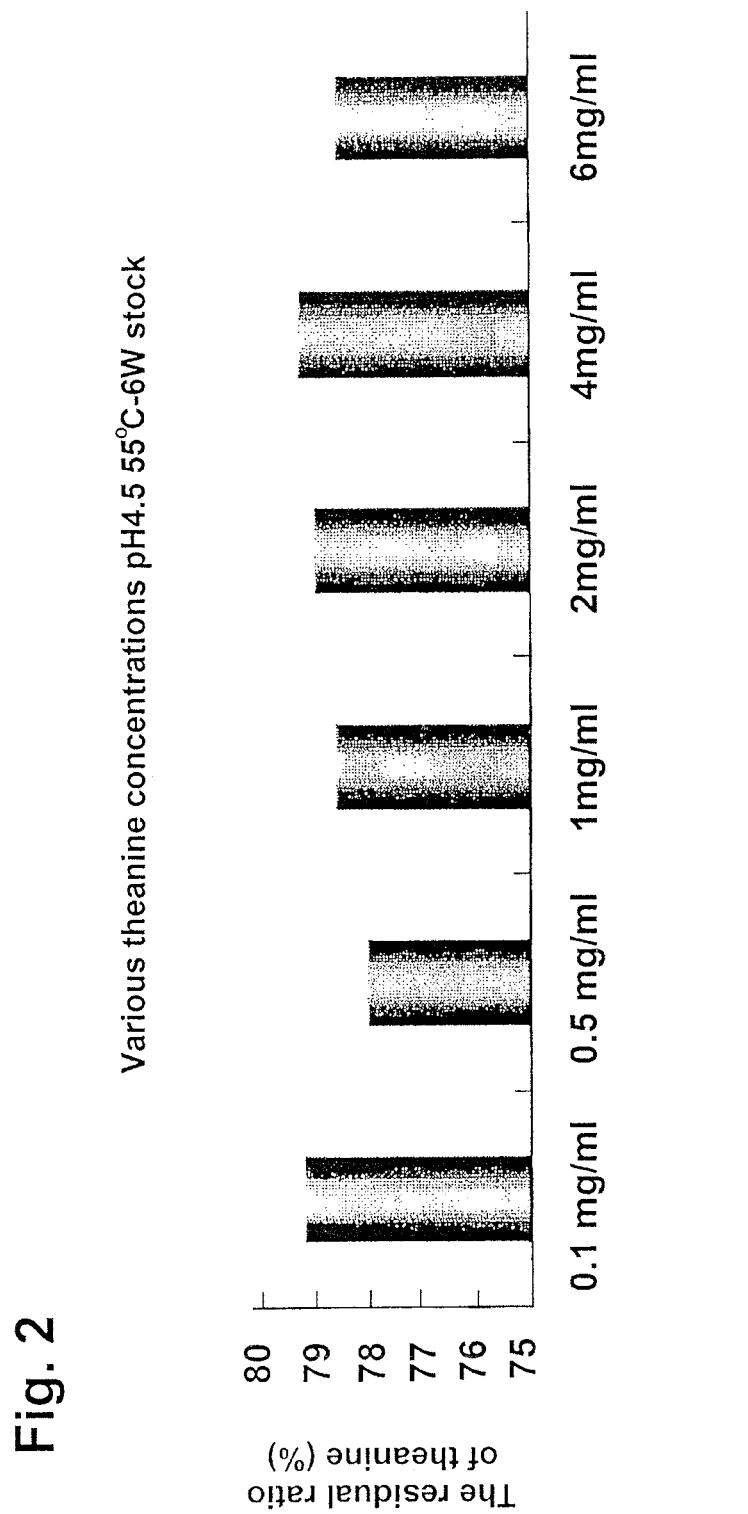
FIG. 2 is a graph showing the residual ratio of theanine after the preservation test with respect to theanine solution of embodiment 8.

Samples of the theanine solution of embodiment 8 were preserved in the manner of preservation test of test example 1 and evaluated by the theanine measurement method described in embodiment 11. FIG. 2 shows theanine content after end of the preservation test.

The axis of abscissas in the figure designates theanine concentration. No changes in the stability with changes in the theanine concentration were recognized as shown in the figure.

<Test Example 4> Comparison of Stability of Theanine with Addition of Pyroglutamic Acid (pH 2.8)

Samples of the theanine solution of embodiment 9 were preserved in the manner of preservation test of test example 1 and evaluated by the theanine measurement method described in embodiment 11. FIG. 3 shows theanine content after end of the preservation test.

The axis of abscissas in the figure designates concentration of pyroglutamic acid relative to theanine content. When no pyroglutamic acid was contained (no addition), a residual ratio of theanine was about 75%. When pyroglutamic acid was added by 0.5% relative to theanine content, the stability of theanine was slightly improved (77%). Furthermore, the residual ratio of theanine was improved with increase in an amount of added pyroglutamic acid relative to theanine content. When the ratio of pyroglutamic acid/theanine was not less than 50%, the residual ratio of theanine was not less than 86%, whereupon remarkable stabilizing action was recognized.

<Test Example 5> Comparison of Stability of Theanine with Addition of Pyroglutamic Acid (pH 7.5)

Samples of the theanine solution of embodiment 10 were preserved in the manner of preservation test of test example 1 and evaluated by the theanine measurement method described in embodiment 11. FIG. 4 shows theanine content after end of the preservation test.

The axis of abscissas in the figure designates concentration of pyroglutamic acid relative to theanine content. When no pyroglutamic acid was contained (no addition), a residual ratio of theanine was about 92%.

On the other hand, when pyroglutamic acid was added by 1.0% relative to theanine content, the stability of theanine was about 94%.

Thus, as in test example 6, stabilization of theanine due to addition of pyroglutamic acid was recognized although the addition was small.

<Test Example 6> Comparison of Stability of Theanine in Beverage with Addition of Pyroglutamic Acid Samples of the beverage of embodiment 12 were preserved in the manner of preservation test of test example 1 and evaluated by the theanine measurement method described in embodiment 11. TABLE 4 shows theanine content after end of the preservation test. In the compared example, 321 mg/100 mL (about 80%) of theanine remained when an initial amount of added theanine was 400 mg/100 mL. On the other hand, 356 mg/100 mL (about 90%) of theanine remained in embodiment 12 of addition of pyroglutamic acid.

TABLE 4

|  | no pyroglutamic acid | pyroglutamic acid 0.1% |
|---|---|---|
| theanine content | 321 mg/100 mL | 356 mg/100 mL |

<Test Example 7> Comparison of Stability of Theanine in Jelly Beverage with Addition of Pyroglutamic Acid Samples of the jelly beverage of embodiment 13 were preserved in the manner of preservation test of test example 1 and evaluated by the theanine measurement method described in embodiment 11. TABLE 5 shows theanine content after end of the preservation test. In the compared example, 164 mg/100 mL (about 82%) of theanine remained after preservation when an initial amount of added theanine was 200 mg/100 mL. On the other hand, 183 mg/100 mL (about 92%) of theanine remained in embodiment 13 of addition of pyroglutamic acid.

TABLE 5

|  | no pyroglutamic acid | pyroglutamic acid 0.1% |
|---|---|---|
| theanine content | 164 mg/100 mL | 183 mg/100 mL |

<Test Example 8> Changes in Theanine Threshold with Addition of Pyroglutamic Acid A sensory evaluation was carried out for changes in the taste threshold of theanine due to pyroglutamic acid. Ten panelists were invited to investigate whether the panelists felt the taste of theanine when pyroglutamic acid was added to a theanine solution. TABLE 6 shows the number of panelists who felt the taste of theanine at respective concentrations of theanine and pyroglutamic acid.

TABLE 6

| theanine | pyroglutamic acid (mg/100 ml) | | | | |
|---|---|---|---|---|---|
| (mg/100 ml) | 0 | 1 | 10 | 50 | 100 |
| 0 | 0 | 0 | 0 | 0 | 0 |
| 100 | 0 | 0 | 0 | 0 | 0 |
| 150 | 8 | 2 | 0 | 0 | 0 |
| 500 | 10 | 3 | 1 | 0 | 0 |
| 1000 | 10 | 5 | 3 | 1 | 0 |

Eight of the ten panelists felt the taste of theanine when the concentration of theanine was 150 mg/100 ml, which value was a threshold of theanine. When 1 mg/100 ml pyroglutamic acid was added to the theanine solution, six of the above eight panelists did not feel the taste of theanine. None of the panelists felt the taste of theanine when 10 mg/100 ml pyroglutamic acid was added to the theanine solution. Even when 100 mg/100 ml pyroglutamic acid was added to the theanine solution with the concentration of 1000 mg/100 ml, the taste of theanine was not felt. Additionally, none of the panelists felt the taste of pyroglutamic acid when 100 mg/100 ml pyroglutamic acid was dissolved into the solution.

<Test Example 9> Changes in Glutamine Threshold with Addition of Pyroglutamic Acid A sensory evaluation was carried out for changes in the taste threshold of glutamine due to pyroglutamic acid. Ten panelists were invited to investigate whether the panelists felt the taste of glutamine when pyroglutamic acid was added to a glutamine solution. The glutamine was made by AJINOMOTO CO., INC. TABLE 7 shows the number of panelists who felt the taste of glutamine at respective concentrations of glutamine and pyroglutamic acid.

TABLE 7

| glutamine | pyroglutamic acid (mg/100 ml) | | | | |
|---|---|---|---|---|---|
| (mg/100 ml) | 0 | 1 | 10 | 50 | 100 |
| 0 | 0 | 0 | 0 | 0 | 0 |
| 150 | 0 | 0 | 0 | 0 | 0 |
| 250 | 7 | 3 | 0 | 0 | 0 |
| 500 | 10 | 4 | 2 | 0 | 0 |
| 1000 | 10 | 5 | 2 | 1 | 0 |

Seven of the ten panelists felt the taste of glutamine when the concentration of glutamine was 250 mg/100 ml, which value was a threshold of glutamine. When 1 mg/100 ml pyroglutamic acid was added to the glutamine solution, four of the above seven panelists did not feel the taste of glutamine. None of the panelists felt the taste of glutamine when 10 mg/100 ml pyroglutamic acid was added to the glutamine solution. Even when 100 mg/100 ml pyroglutamic acid was added to the glutamine solution with the concentration of 1000 mg/100 ml, the taste of glutamine was not felt. Additionally, none of the panelists felt the taste of pyroglutamic acid when 100 mg/100 ml pyroglutamic acid was dissolved into the solution.

<Test Example 10> Changes in Glutamic Acid Threshold with Addition of Pyroglutamic Acid A sensory evaluation was carried out for changes in the taste threshold of glutamic acid due to pyroglutamic acid. Ten panelists were invited to investigate whether the panelists felt the taste of glutamic acid when pyroglutamic acid was added to a glutamine solution. The glutamic acid was made by AJINOMOTO CO., INC. TABLE 8 shows the number of panelists who felt the taste of glutamic acid at respective concentrations of glutamic acid and pyroglutamic acid.

TABLE 8

| glutamic acid | pyroglutamic acid (mg/100 ml) | | | | |
|---|---|---|---|---|---|
| (mg/100 ml) | 0 | 1 | 10 | 50 | 100 |
| 0 | 0 | 0 | 0 | 0 | 0 |
| 1 | 0 | 0 | 0 | 0 | 0 |
| 5 | 9 | 4 | 2 | 0 | 0 |
| 10 | 10 | 5 | 2 | 0 | 0 |
| 20 | 10 | 7 | 5 | 3 | 0 |

Nine, of the ten panelists felt the taste of glutamine when the concentration of glutamic acid was 5 mg/100 ml, which value was a threshold of glutamic acid. When 1 mg/100 ml pyroglutamic acid was added to the glutamic acid solution, five of the above nine panelists did not feel the taste of glutamic acid. None of the panelists felt the taste of glutamic acid when 50 mg/100 ml pyroglutamic acid was added to the glutamine solution. Even when 100 mg/100 ml pyroglutamic acid was added to the glutamic acid solution with the concentration of 100 mg/100 ml, the taste of glutamine was not felt. Additionally, none of the panelists felt the taste of pyroglutamic acid when 100 mg/100 ml pyroglutamic acid was dissolved into the solution.

<Test Example 11> Changes in Valine Threshold with Addition of Pyroglutamic Acid and Theanine A sensory evaluation was carried out for changes in the taste threshold of glutamine due to pyroglutamic acid. Ten panelists were invited to investigate whether the panelists felt the taste of glutamine when pyroglutamic acid was added to a glutamine solution. The glutamine was made by AJINOMOTO CO., INC. TABLE 7 shows the number of panelists who felt the taste of glutamine at respective concentrations of glutamine and pyroglutamic acid.

TABLE 9

| valine | pyroglutamic acid/ theanine (mg/100 ml) | | | | |
|---|---|---|---|---|---|
| (mg/100 ml) | 0 | 1 | 10 | 50 | 100 |
| 0 | 0 | 0 | 0 | 0 | 0 |
| 100 | 0 | 0 | 0 | 0 | 0 |
| 150 | 8 | 2 | 0 | 0 | 0 |
| 500 | 10 | 3 | 1 | 0 | 0 |
| 1000 | 10 | 5 | 3 | 1 | 0 |

Eight of the ten panelists felt the bitter taste of valine when the concentration of valine was 150 mg/100 ml, which value was a threshold of valine. When 1 mg/100 ml mixture of glutamic acid and theanine was added to the valine solution, six of the above eight panelists did not feel the bitter taste of valine. None of the panelists felt the bitter taste of valine when 10 mg/100 ml mixture was added to the valine solution. Even when 100 mg/100 ml mixture was added to the Valine solution with the concentration of 1000 mg/100 ml, the bitter taste of valine was not felt. Additionally, none of the panelists felt the taste of mixture of pyroglutamic acid and theanine when 100 mg/100 ml pyroglutamic acid was dissolved into the solution.

<Test Example 12> Changes in Leucine Threshold with Addition of Pyroglutamic Acid and Theanine A sensory evaluation was carried out for changes in the taste threshold of leucine due to pyroglutamic acid and theanine. Ten panelists were invited to investigate whether the panelists felt the bitter taste of leucine when pyroglutamic acid and theanine were added to a leucine solution. The leucine was made by AJINOMOTO CO., INC. TABLE 10 shows the number of panelists who felt the taste of leucine at respective concentrations of mixtures (mixing weight ratio: pyroglutamic acid:theanine=1:50) of leucine, pyroglutamic acid and theanine.

TABLE 10

| leucine | pyroglutamic acid/ theanine (mg/100 ml) | | | | |
|---|---|---|---|---|---|
| (mg/100 ml) | 0 | 1 | 10 | 50 | 100 |
| 0 | 0 | 0 | 0 | 0 | 0 |
| 200 | 0 | 0 | 0 | 0 | 0 |
| 380 | 5 | 1 | 0 | 0 | 0 |
| 500 | 7 | 2 | 0 | 0 | 0 |
| 1000 | 10 | 3 | 1 | 0 | 0 |

Five of the ten panelists felt the bitter taste of leucine when the concentration of leucine was 380 mg/100 ml, which value was a threshold of leucine. When 1 mg/100 ml mixture of pyroglutamic acid and theanine was added to the leucine solution, four of the above five panelists did not feel the bitter taste of leucine. None of the panelists felt the bitter taste of leucine when 10 mg/100 ml mixture was added to the leucine solution. Even when 100 mg/100 ml mixture was added to the leucine solution with the concentration of 1000 mg/100 ml, the bitter taste of leucine was not felt. Additionally, none of the panelists felt the taste of mixture of pyroglutamic acid and theanine when 100 mg/100 ml mixture of pyroglutamic acid and theanine was dissolved into the solution.

<Test Example 13> Changes in Isoleucine Threshold with Addition of Pyroglutamic Acid and Theanine A sensory evaluation was carried out for changes in the taste threshold of isoleucine due to pyroglutamic acid and theanine. Ten panelists were invited to investigate whether the panelists felt the bitter taste of isoleucine when pyroglutamic acid and theanine were added to an isoleucine solution. The isoleucine was made by AJINOMOTO CO., INC. TABLE 11 shows the number of panelists who felt the bitter taste of isoleucine at respective concentrations of mixtures (mixing weight ratio: pyroglutamic acid:theanine=1:50) of isoleucine, pyroglutamic acid and theanine.

TABLE 11

| isoleucine | pyroglutamic acid/ theanine (mg/100 ml) | | | | |
|---|---|---|---|---|---|
| (mg/100 ml) | 0 | 1 | 10 | 50 | 100 |
| 0 | 0 | 0 | 0 | 0 | 0 |
| 50 | 0 | 0 | 0 | 0 | 0 |
| 90 | 7 | 4 | 1 | 0 | 0 |
| 200 | 9 | 4 | 1 | 0 | 0 |
| 500 | 10 | 6 | 4 | 3 | 0 |

Seven of the ten panelists felt the bitter taste of isoleucine when the concentration of isoleucine was 90 mg/100 ml, which value was a threshold of leucine. When 1 mg/100 ml mixture of pyroglutamic acid and theanine was added to the isoleucine solution, three of the above seven panelists did not feel the bitter taste of isoleucine. None of the panelists felt the bitter taste of isoleucine when 50 mg/100 ml mixture was added to the isoleucine solution. Even when 100 mg/100 ml mixture was added to the isoleucine solution with the concentration of 500 mg/100 ml, the bitter taste of isoleucine was not felt. Additionally, none of the panelists felt the taste of mixture of pyroglutamic acid and theanine when 100 mg/100 ml pyroglutamic acid was dissolved into the solution.

<Test Example 14> Changes in Acesulfame K Threshold with Addition of Pyroglutamic Acid and Theanine A sensory evaluation was carried out for changes in the taste threshold of acesulfame K due to pyroglutamic acid and theanine. Ten panelists were invited to investigate whether the panelists felt the taste of acesulfame K when pyroglutamic acid and theanine were added to an acesulfame K solution. The acesulfame K was made by TAKEDA-KIRIN FOODS CORPORATION. TABLE 12 shows the number of panelists who felt the bitter taste of acesulfame K at respective concentrations of mixtures (mixing weight ratio: pyroglutamic acid:theanine=1:50) of isoleucine, pyroglutamic acid and theanine.

TABLE 12

| acesulfame K | pyroglutamic acid/ theanine (mg/100 ml) | | | | |
|---|---|---|---|---|---|
| (mg/100 ml) | 0 | 1 | 10 | 50 | 100 |
| 0 | 0 | 0 | 0 | 0 | 0 |
| 1 | 0 | 0 | 0 | 0 | 0 |
| 3 | 7 | 3 | 0 | 0 | 0 |
| 5 | 9 | 4 | 1 | 0 | 0 |
| 10 | 10 | 6 | 2 | 1 | 0 |

Seven of the ten panelists felt the bitter taste of acesulfame K when the concentration of acesulfame K was 3 mg/100 ml, which value was a threshold of acesulfame K. When 1 mg/100 ml mixture of pyroglutamic acid and theanine was added to the acesulfame K solution, four of the above seven panelists did not feel the bitter taste of acesulfame K. None of the panelists felt the bitter taste of acesulfame K when 10 mg/100 ml mixture was added to the acesulfame K solution. Even when 100 mg/100 ml mixture was added to the acesulfame K solution with the concentration of 10 mg/100 ml, the bitter taste of acesulfame K was not felt. Additionally, none of the panelists felt the taste of mixture of pyroglutamic acid and theanine when 100 mg/100 ml mixture of pyroglutamic acid and theanine was dissolved into the solution.

<Test Example 15> Changes in Aspartame Threshold with Addition of Pyroglutamic Acid and Theanine A sensory evaluation was carried out for changes in the taste threshold of aspartame due to pyroglutamic acid and theanine. Ten panelists were invited to investigate whether the panelists felt the taste of aspartame when pyroglutamic acid and theanine were added to an aspartame solution. The aspartame was made by AJINOMOTO CO., INC. TABLE 13 shows the number of panelists who felt the bitter taste of aspartame at respective concentrations of mixtures (mixing weight ratio: pyroglutamic acid:theanine=1:50) of aspartame, pyroglutamic acid and theanine.

TABLE 13

| aspartame | pyroglutamic acid/ theanine (mg/100 ml) | | | | |
|---|---|---|---|---|---|
| (mg/100 ml) | 0 | 1 | 10 | 50 | 100 |
| 0 | 0 | 0 | 0 | 0 | 0 |
| 1 | 0 | 0 | 0 | 0 | 0 |
| 3 | 7 | 4 | 0 | 0 | 0 |
| 5 | 10 | 2 | 1 | 0 | 0 |
| 10 | 10 | 4 | 3 | 1 | 0 |

Seven of the ten panelists felt the bitter taste of aspartame when the concentration of aspartame was 3 mg/100 ml, which value was a threshold of aspartame. When 1 mg/100 ml mixture of pyroglutamic acid and theanine was added to the aspartame solution, three of the above seven panelists did not feel the bitter taste of aspartame. None of the panelists felt the bitter taste of aspartame when 10 mg/100 ml mixture was added to the aspartame solution. Even when 100 mg/100 ml mixture was added to the aspartame solution with the concentration of 10 mg/100 ml, the bitter taste of aspartame was not felt. Additionally, none of the panelists felt the taste of mixture of pyroglutamic acid and theanine when 100 mg/100 ml mixture of pyroglutamic acid and theanine was dissolved into the solution.

<Test Example 16> Changes in L-Phenylalanine Threshold with Addition of Pyroglutamic Acid and Theanine A sensory evaluation was carried out for changes in the taste threshold of L-phenylalanine due to pyroglutamic acid and theanine. Ten panelists were invited to investigate whether the panelists felt the taste of L-phenylalanine when pyroglutamic acid and theanine were added to an L-phenylalanine solution. The L-phenylalanine was made by AJINOMOTO CO., INC. TABLE 14 shows the number of panelists who felt the bitter taste of L-phenylalanine at respective concentrations of mixtures (mixing weight ratio: pyroglutamic acid:theanine=1:50) of aspartame, pyroglutamic acid and theanine.

TABLE 14

| L-phenylalanine (mg/100 ml) | pyroglutamic acid/ theanine (mg/100 ml) | | | | |
|---|---|---|---|---|---|
| | 0 | 1 | 10 | 50 | 100 |
| 0 | 0 | 0 | 0 | 0 | 0 |
| 10 | 0 | 0 | 0 | 0 | 0 |
| 30 | 8 | 1 | 0 | 0 | 0 |
| 50 | 10 | 3 | 1 | 0 | 0 |
| 100 | 10 | 5 | 3 | 1 | 0 |

Eight of the ten panelists felt the bitter taste of L-phenylalanine when the concentration of L-phenylalanine was 30 mg/100 ml, which value was a threshold of L-phenylalanine. When 1 mg/100 ml mixture of pyroglutamic acid and theanine was added to the L-phenylalanine solution, seven of the above eight panelists did not feel the bitter taste of L-phenylalanine. None of the panelists felt the bitter taste of L-phenylalanine when 10 mg/100 ml mixture was added to the L-phenylalanine solution. Even when 100 mg/100 ml mixture was added to the L-phenylalanine solution with the concentration of 100 mg/100 ml, the bitter taste of L-phenylalanine was not felt. Additionally, none of the panelists felt the taste of mixture of pyroglutamic acid and theanine when 100 mg/100 ml mixture of pyroglutamic acid and theanine was dissolved into the solution.

<Test Example 17> Changes in Albumen Peptide Threshold with Addition of Pyroglutamic Acid and Theanine A sensory evaluation was carried out for changes in the bitter taste threshold of albumen peptide due to pyroglutamic acid and theanine. Ten panelists were invited to investigate whether the panelists felt the bitter taste of albumen peptide when pyroglutamic acid and theanine were added to an albumen peptide solution. Trade name, "RunPep" made by Pharma Foods International Co., Ltd. was used as the albumen peptide. TABLE 15 shows the number of panelists who felt the bitter taste of albumen peptide at respective concentrations of mixtures (mixing weight ratio: pyroglutamic acid:theanine=1:50) of albumen peptide, pyroglutamic acid and theanine.

TABLE 15

| albumen peptide (mg/100 ml) | pyroglutamic acid/ theanine (mg/100 ml) | | | | |
|---|---|---|---|---|---|
| | 0 | 1 | 10 | 50 | 100 |
| 0 | 0 | 0 | 0 | 0 | 0 |
| 100 | 0 | 0 | 0 | 0 | 0 |
| 1000 | 9 | 4 | 0 | 0 | 0 |
| 3000 | 10 | 5 | 0 | 0 | 0 |
| 5000 | 10 | 7 | 4 | 2 | 0 |

Nine of the ten panelists felt the bitter taste of albumen peptide when the concentration of albumen peptide was 1000 mg/100 ml, which value was a threshold of albumen peptide. When 1 mg/100 ml mixture of pyroglutamic acid and theanine was added to the albumen peptide solution, five of the above nine panelists did not feel the bitter taste of albumen peptide. None of the panelists felt the bitter taste of albumen peptide when 10 mg/100 ml mixture was added to the albumen peptide solution. Even when 100 mg/100 ml mixture was added to the albumen peptide solution with the concentration of 500 mg/100 ml, the bitter taste of albumen peptide was not felt. Additionally, none of the panelists felt the taste of mixture of pyroglutamic acid and theanine when 100 mg/100 ml mixture of pyroglutamic acid and theanine was dissolved into the solution.

Thus, according to the present invention, the hydrated food can be provided in which theanine content can stably be maintained even when the hydrated food is preserved for a long period of time. Furthermore, the hydrated food can be provided in which the taste threshold of the food can be improved and the peculiar taste can be flavored.

<Specific Forms>

Specific forms of the present invention are as follows:

(1) A hydrated food characterized in that theanine is L-theanine;

(2) A hydrated food characterized in that the theanine content ranges from about 0.03 mg/mL to about 200 mg/mL, and the pyroglutamine content ranges from about 1% to about 200% relative to the theanine content;

(3) A hydrated food characterized in that the theanine content ranges from about 1.5 mg/ml, to about 200 mg/mL, and the pyroglutamine content ranges from about 1% to about 200% relative to the theanine content;

(4) A hydrated food characterized in that in the above (2), pH ranges from about 2.8 to about 7.5;

(5) A hydrated food characterized in that the hydrated food is a juice; and (6) A hydrated food characterized in that the hydrated food is a jelly beverage.

The invention claimed is:

1. A method for keeping theanine stable and a non-theanine-taste in a beverage, the method comprising: preparing the beverage containing pyroglutamic acid and theanine, wherein the pyroglutamic acid content is in the range of from about 0.01 mg/mL to about 1 mg/mL and the theanine content is in the range of from about 0.1 mg/mL to about 10 mg/mL, wherein pyroglutamic acid/theanine is at least about 0.1%.

2. The method according to claim 1, wherein the pH of the beverage is in the range of from about 2.8 to about 4.5.

3. A method for keeping theanine stable and a non-theanine-taste in a beverage, the method comprising: preparing the beverage containing pyroglutamic acid, theanine and additive, wherein the pyroglutamic acid content is in the range of from about 0.01 mg/mL to about 1 mg/mL, the theanine content is in the range of from about 0.1 mg/mL to about 10 mg/mL, and the additive is selected from the group consisting of valine, leucine, isoleucine, acesulfame K, aspartame, L-phenylalanine, and albumin peptide, wherein pyroglutamic acid/theanine is at least about 0.1%.

4. The method according to claim 3, wherein the pH of the beverage is from about 2.8 to about 4.5.

* * * * *